United States Patent [19]
Owens et al.

[11] Patent Number: 5,386,828
[45] Date of Patent: Feb. 7, 1995

[54] GUIDE WIRE APPARATUS WITH LOCATION SENSING MEMBER

[75] Inventors: Robert C. Owens, Forest Lake; Theodore A. Johnson, St. Paul, both of Minn.

[73] Assignee: SIMS Deltec, Inc., St. Paul, Minn.

[21] Appl. No.: 108,177

[22] Filed: Aug. 17, 1993

Related U.S. Application Data

[63] Continuation of Ser. No. 813,881, Dec. 23, 1991, abandoned.

[51] Int. Cl.⁶ .............................................. A61B 5/05
[52] U.S. Cl. .................. 128/653.1; 128/772; 600/13; 604/164; 604/282
[58] Field of Search ............... 128/772, 657, 658, 737, 128/653.1; 604/158, 164, 280, 282, 166, 170; 600/13

[56] References Cited

U.S. PATENT DOCUMENTS

| | | |
|---|---|---|
| 3,452,742 | 7/1969 | Muller . |
| 3,547,103 | 12/1970 | Cook . |
| 3,625,200 | 12/1971 | Muller . |
| 3,749,086 | 7/1973 | Kline et al. . |
| 3,922,378 | 11/1975 | Kline ................... 128/772 |
| 3,973,556 | 8/1976 | Fleischhacker et al. . |
| 4,020,829 | 5/1977 | Willson et al. . |
| 4,080,706 | 3/1978 | Heilman et al. . |
| 4,173,228 | 11/1979 | Van Steenwyk et al. ....... 128/653.1 |
| 4,248,236 | 2/1981 | Linder . |
| 4,344,436 | 8/1982 | Kubota . |
| 4,402,328 | 9/1983 | Doring . |
| 4,405,314 | 9/1983 | Cope . |
| 4,431,005 | 2/1984 | McCormick ........... 128/656 |
| 4,509,945 | 4/1985 | Kramann et al. . |
| 4,534,363 | 8/1985 | Gold . |
| 4,552,157 | 11/1985 | Littleford . |
| 4,602,645 | 7/1986 | Barrington et al. . |
| 4,676,249 | 6/1987 | Arenas et al. ............ 128/657 |
| 4,771,788 | 9/1988 | Millar . |
| 4,790,331 | 12/1988 | Okada et al. . |
| 4,796,642 | 1/1989 | Harris ................... 128/772 |
| 4,811,743 | 3/1989 | Stevens . |
| 4,839,020 | 6/1989 | Yamaguchi et al. . |
| 4,854,330 | 8/1989 | Evans, III et al. . |
| 4,860,757 | 8/1989 | Lynch et al. . |
| 4,884,573 | 12/1989 | Wijay et al. . |
| 4,899,757 | 2/1990 | Pope, Jr. et al. . |
| 4,905,698 | 3/1990 | Strohl, Jr. et al. ........ 128/737 |
| 4,917,094 | 4/1990 | Lynch et al. . |
| 4,925,445 | 5/1990 | Sakamoto et al. ........ 604/95 |
| 4,926,858 | 5/1990 | Gifford, III et al. . |
| 4,932,419 | 6/1990 | de Toledo . |
| 4,940,062 | 7/1990 | Hampton et al. . |
| 5,005,592 | 4/1991 | Cartmell ............... 128/899 |
| 5,040,543 | 8/1991 | Badera et al. ............ 128/772 |
| 5,099,845 | 3/1992 | Besz et al. ............. 128/653.1 |

FOREIGN PATENT DOCUMENTS

| | | |
|---|---|---|
| 091577 | 10/1983 | European Pat. Off. . |
| 320623 | 6/1989 | European Pat. Off. . |
| 0355996 | 2/1990 | European Pat. Off. . |
| WO88/00810 | 2/1988 | WIPO . |

*Primary Examiner*—Stephen C. Pellegrino
*Assistant Examiner*—Guy V. Tucker
*Attorney, Agent, or Firm*—Merchant, Gould, Smith, Edell, Welter & Schmidt

[57] ABSTRACT

The invention is directed to a guide wire apparatus and a method for detecting the location of a guide wire within the body of a patient. The apparatus includes a guide wire with an internally-housed sensing member. The guide wire assembly is structured to provide the response, maneuverability and tactile feel comparable to conventional guide wire devices. The apparatus is useful in medical treatments and diagnoses such as angioplasty or catheterization procedures, for detecting obstructions within a blood vessel of a patient, and the like.

20 Claims, 4 Drawing Sheets

GUIDE WIRE APPARATUS WITH LOCATION SENSING MEMBER

This application is a continuation application of Ser. No. 07/813,881, filed Dec. 23, 1991, now abandoned.

BACKGROUND OF THE INVENTION

Catheters are used in conjunction with various procedures to diagnose and treat systems of the body, particularly the vascular system. Guide wires are used to aid in the insertion of catheters into the body and to evaluate the vessel along which the catheter will travel. In general, a guide wire is inserted into a body system such as a blood vessel and the vessel is probed with the guide wire. The catheter is slipped over the guide wire and the guide wire is withdrawn. The catheter is then eased through the vessel to the desired location.

For proper manipulation and control of the guide wire during insertion, the operator must be able to tactilely feel the end of the guide wire within the vessel. For selectively placing a guide wire in a particular corridor of a body system such as a blood vessel, guide wires with flexible end portions are employed. J-shaped guide wires are particularly useful for maneuvering through curves and junctures of branched portions of a body system.

To position the guide wire at a particular location within the body, it is useful to have a means of detecting the location of the tip of the guide wire. To this end, guide wires may be marked at intervals along their length, wound with a dense metal such as platinum, gold or tungsten to provide radiopacity for detection by fluoroscopy, or other such marking technique. At present, however, there are no guide wires with self-contained sensor components that would permit determination of the location of the guide wire tip after it has been inserted into the patient without the use of fluoroscopy.

It would be desirable to have a guide wire with an internally-housed sensor for locating the distal section of the guide wire within the body. It would also be desirable to design such a guide wire to have the tactile response to enable the operator to manipulate and sense the progress of the leading end of the guide wire during insertion and placement in the body, particularly through branched channels of a the cardiovascular system.

Therefore, an object of the invention is to provide a guide wire apparatus with an internally-housed sensor element for detection of the guide wire position in the body, a further object is to provide a guide wire with a sensor that has the tactile response of a conventional non-sensor guide wire. Another object is to provide a method of using the guide wire apparatus for detecting obstructions in the body, as for example, the vascular system.

SUMMARY OF THE INVENTION

These and other goals are achieved by the present invention which is directed to a guide wire apparatus which will allow determination of its location when it is inserted within the body of a patient, and a method for its use.

The guide wire apparatus of the invention includes a guide wire and sensing member for detecting the location of the guide wire distal end position in the body. The guide wire has a channel or lumen extending at least part of its length, and proximal, center and distal portions. The lumen of the guide wire is dimensioned to facilitate insertion and housing of the sensing member.

The sensing member is an elongate metal core with proximal, center and distal sections, and a sensor element. Preferably, the metal core is tapered at the center section such that the diameter of about the midpoint of the center section is narrower than both the distal and proximal sections. The sensor element is formed by a current conducting wire wrapped around at least part of the metal core distal section. The sensing member may be coated with a protective covering material.

The construction of the guide wire, the sensing member, or both, provides the guide wire apparatus with a flexibility factor such that the combination of the guide wire and sensing member results in a guide wire apparatus with a tactile feel, response and maneuverability within the body of a patient, particularly the vascular system, comparable to that of conventional guide wires without internally-housed sensors. Preferably, the desired tactile response and maneuverability of the guide wire apparatus may be provided by constructing the sensing member with a tapered area at the center section of the metal core.

The invention may further include a means for generating and measuring an electromagnetic current in the sensor element. The generation is accomplished by an external means for producing an electromagnetic energy field. The measurement is accomplished by an electronic controller which measures the sensor current generated by the field. The apparatus may further include means for transmitting current (e.g., alternating current) to the electromagnetic energy field generating means. In one embodiment, the electronic controller may measure the intensity or amplitude of the current in the sensor element. With this embodiment, the location of the distal section of the guide wire within the body is determined by detecting the strength or magnitude of the sensor current as the external means for generating the field is moved over the body (see, for example, U.S. Pat. No. 4,173,228 to Van Steenwyk, the disclosure of which is incorporated herein by reference). In an alternative embodiment, the electronic controller may be designed to detect a phase transition of the sensor current as the external means for generating the field is moved over the approximate location of the guide wire distal section within the body (see, for example, U.S. Pat. No. 4,905,698 to Strohl et al., incorporated by reference herein (issued Mar. 6, 1990), subject of a Reexamination issued Oct. 1, 1991.

The invention further includes a method of detecting the location of a guide wire and/or an obstruction in the body of a patient using the guide wire apparatus described herein. The method includes inserting the guide wire apparatus into the body of the patient, advancing the apparatus to the desired site within the body, and detecting the location of the sensor element of the guide wire apparatus. An obstruction is sensed by the tactile response of the guide wire as it is advanced within the body. The location of the obstruction is determined by detecting the location of the sensor element.

BRIEF DESCRIPTION OF THE DRAWINGS

Throughout the following views, reference numerals will be used on the drawings, and the same reference numerals will be used throughout the several views and in the description to indicate same or like parts of the inventions.

DETAILED DESCRIPTION OF THE INVENTION

Figure 1:
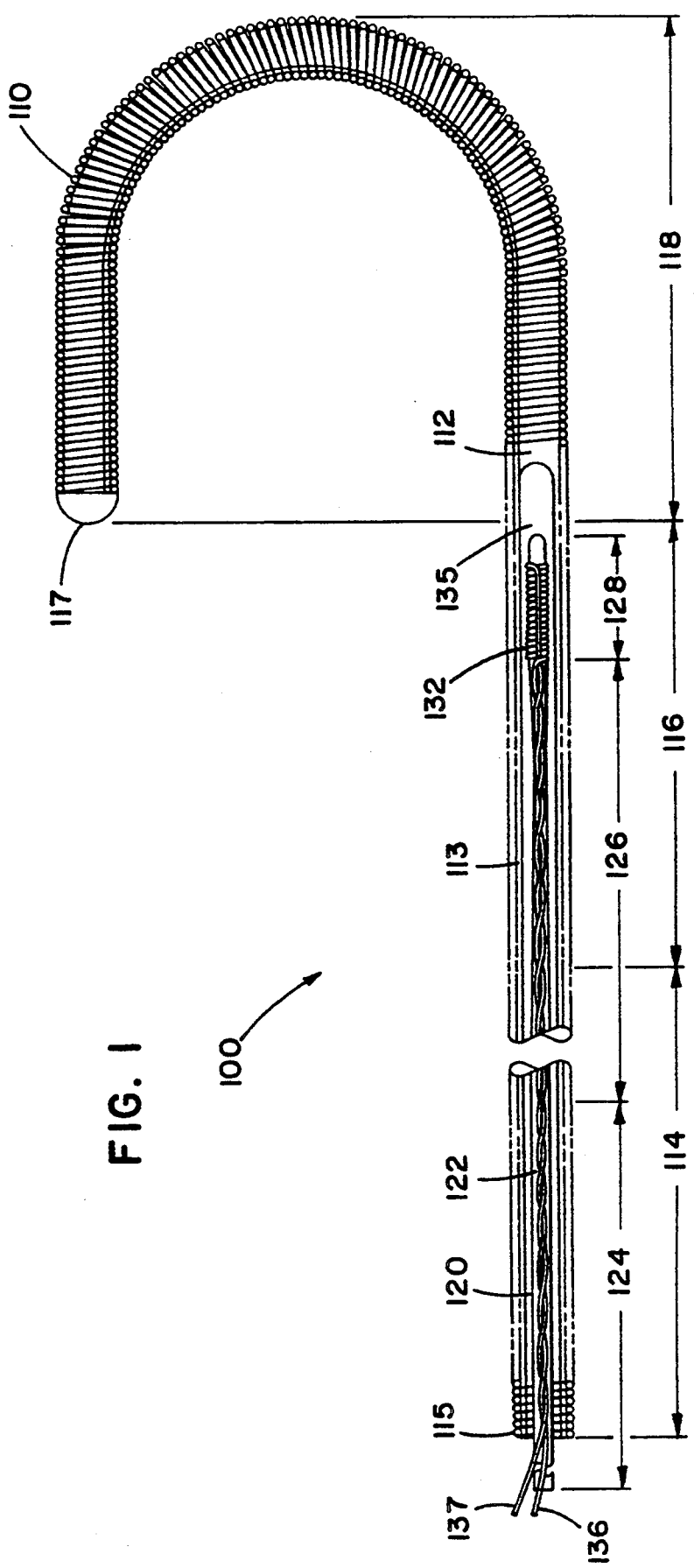
FIG. 1 illustrates a fragmentary, cross-sectional side view of a guide wire assembly in accordance with the present invention.

The guide wire apparatus of the invention is made of a guide wire portion, and a sensing member for locating the distal end of the guide wire in the body.

The guide wire has proximal, center and distal portions, and a lumen extending at least part of the length of the guide wire. Preferably, the guide wire is a helically coiled wire with elongate proximal and center portions, and a shorter distal portion. In the coiled configuration, the guide wire may include an internal safety wire, with a diameter of about 0.05 to 0.5 mm, preferably about 0.08 to 0.2 mm, extending the length of the guide wire and coupled at the distal and proximal ends of the guide wire to prevent longitudinal elongation of the coiled wire.

The distal portion of the guide wire is the leading end of the guide wire and is constructed to be easily flexed. The distal portion is the end of the guide wire to be inserted into the body of a patient. Consequently, when the guide wire apparatus is advanced within the body and encounters a peritoneal blood vessel, the tip of the guide wire does not cause puncture or perforation of the blood vessel wall. Preferably, the tip of the guide wire is rounded. The resiliency of the distal portion also allows the guide wire apparatus to be readily maneuvered through curves and branches within the body system in which the apparatus is used. The proximal and center portions of the guide wire are capable of flexing but are comparatively stiffer than the distal portion. To provide these differing levels of stiffness, the proximal and center portions of the guide wire may be formed, for example, of more tightly coiled wire than the distal portion, of wire that has less flexibility than that forming the distal portion, or wire that has a larger diameter than that of the distal portion.

Although there is no precise juncture between the proximal and center portions, in general, these two portions of the guide wire are approximately equal in length. The proximal and center portions have a combined length effective for the distal portion of the guide wire to reach a desired site within the body system being examined. Preferably, the combined length of the proximal and center portions is about 70 to 80 cm, more preferably about 75 cm. The juncture between the center and distal portions of the guide wire may be gradual or abrupt. The distal portion of the guide wire has a length effective to facilitate maneuvering of the guide wire by the operator through curves and branches of a body system. The length of the distal portion of the guide wire is preferably about 0.5 to 3 cm long, more preferably about 1 to 2 cm long.

The distal or leading end of the guide wire may be of any shape suitable to allow the guide wire to be inserted into the body of the patient and advanced within the body system to the desired site. The distal end may have a configuration that is straight, J-shaped, L-shaped, and the like, with a J-shaped configuration being preferred.

The sensing member of the guide wire apparatus includes a sensor element formed of a current conducting wire wound around a metal core. The metal core has a proximal, central and distal section. In cross-section, the metal core may be flat, round, octagonal, or other shape, and may be solid or hollow. Preferably, the metal core is a solid wire.

The metal core of the sensing member may be made of any suitable magnetically permeable metal material which will interact with the electromagnetic field flux to cause a strong generated current within the sensor element. Examples of suitable materials for the metal core include iron, nickel, cobalt, manganese, chromium, stainless steel, and the like, alone or in combination. Preferably, the metal core is composed of a stainless steel that has magnetic properties as a result of the presence of ferritic particles. A suitable example would be an American Iron and Steel Institute (AISI) 400 series stainless steel. The stainless steel core may also be covered with an outer layer of iron to further enhance its magnetic properties. In another embodiment, the metal core may have a distal section formed of an iron core that is bonded to a stainless steel core forming the center and proximal sections.

When the sensing member is assembled into the lumen of the guide wire, the resulting guide wire apparatus possesses a level of flexibility yet stiffness comparable to the response, maneuverability and tactile feel of a guide wire without an internal sensor housed therein, like those of the traditional or conventional guide wire devices used in diagnostic and treatment procedures. In particular, the guide wire apparatus has an appropriate combination of stiffness and bendability to provide the desired control and flexibility for use in medical applications, such as angioplasty or catheterization procedures, for detecting obstructions within a channel of a body organ such as a blood vessel of a patient.

It is preferred that the desired tactile response and maneuverability is provided in part by the construction of the guide wire, the sensing member, or both. Preferably, the metal core of the sensing member is constructed to provide the guide wire apparatus with the desired flexibility. For example, the center section of the metal core of the sensing member may be tapered so that the diameter of about its mid-point is less than the diameter of either the distal or proximal sections of the metal core. The tapered configuration of the metal core provides the sensing member with a flexibility or bendability factor to provide, at least in part, the desired level of flexibility and stiffness in the guide wire apparatus.

A current conducting wire is preferably wound around the distal section of the metal core in one or more overlying layers, preferably two layers, to form the sensor element. The current conducting wire is composed of a fine wire with a diameter of about 0.04 to 0.08 mm, with about 0.05 mm being preferred. The distal section of the metal core is of a length suitable to accommodate an effective amount of the conducting wire to form the sensor element. In a preferred embodiment, the sensor element includes about 250–300 winds, more preferably about 280 winds, of the conducting wire in a double layer over the distal section. The current conducting wire may be composed of any suitable material capable of conducting a current, as for example, the noble metals such as copper, silver, gold, platinum, palladium, or other like material, copper being most preferred. The ends of the current conducting wire are connected by two lead wires to the electronic controller. Preferably, the ends of the current conducting wire extend along the length of the metal core and connect with the lead wires at the proximal end of the apparatus.

To protect the sensor element from damage, the sensing member may be coated with a protective covering material, preferably a flexible, non-toxic, insulating material. Suitable coating materials include polymer materials such as polyurethane, polyethylene, polyvinyl chloride, nylon (polyamide), teflon (Tetrafluoroethylene (TFE) fluorocarbon polymers, an example of which is polytetrafluoroethylene (trademarked as Teflon, a registered mark of The du Pont Company, Wilmington, Del. (polyperfluoroolefin), or a polyester material. The polymer material may be applied by any suitable method which will provide a thin covering layer, preferably about 0.05 to 0.2 mm thick, more preferably about 0.1 to 0.15 mm thick, on the surface of the sensing member without altering or damaging the sensor element.

The diameters of the proximal, center and distal sections of the metal core are adapted to fit the sensing member having an applied coating layer within the lumen of the guide wire. In a preferred embodiment, the diameter of the distal section of metal core with a layer of conducting wire is about 0.3 to 1 mm, more preferably about 0.5 to 0.8 mm; and the diameter of the proximal core section is about 0.2 to 0.8 mm, more preferably about 0.3 to 0.5 mm. In a preferred embodiment of the sensing member, the diameter of the mid-point of the center core section of the metal core is about 0.1 to 0.4 mm, more preferably about 0.2 to 0.3 mm.

The sensing member is housed within the lumen of the guide wire, preferably with the proximal end of the sensing member co-terminus with the proximal end of the guide wire. The lengths of the metal core and of the lumen of the guide wire are sufficient to place the sensor element in the area of the center portion of the guide wire at or near the adjoining distal portion.

Figure 2:
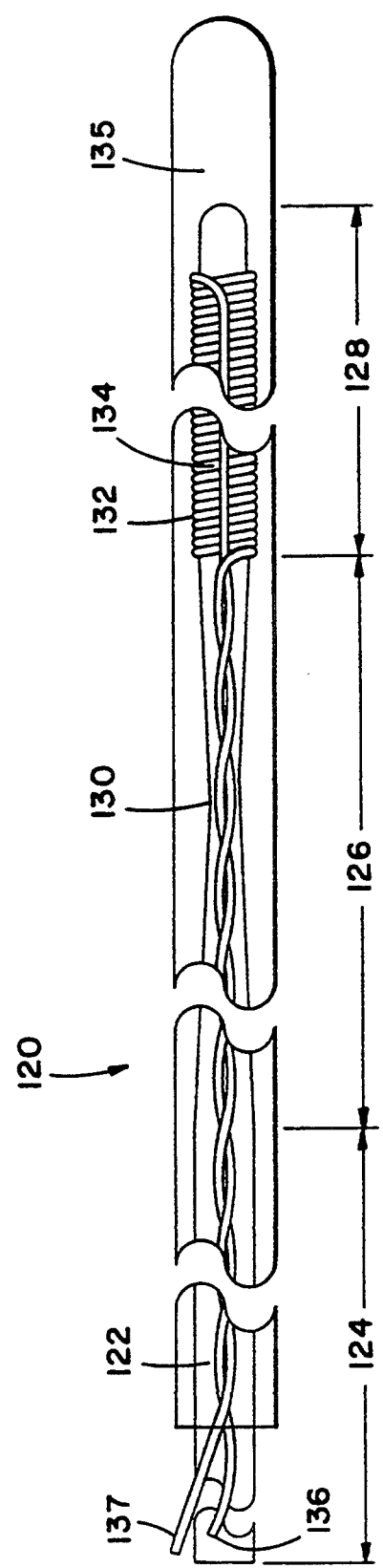
FIG. 2 is a fragmentary, cross-sectional view of the sensor element illustrated in FIG. 1.
Figure 3:
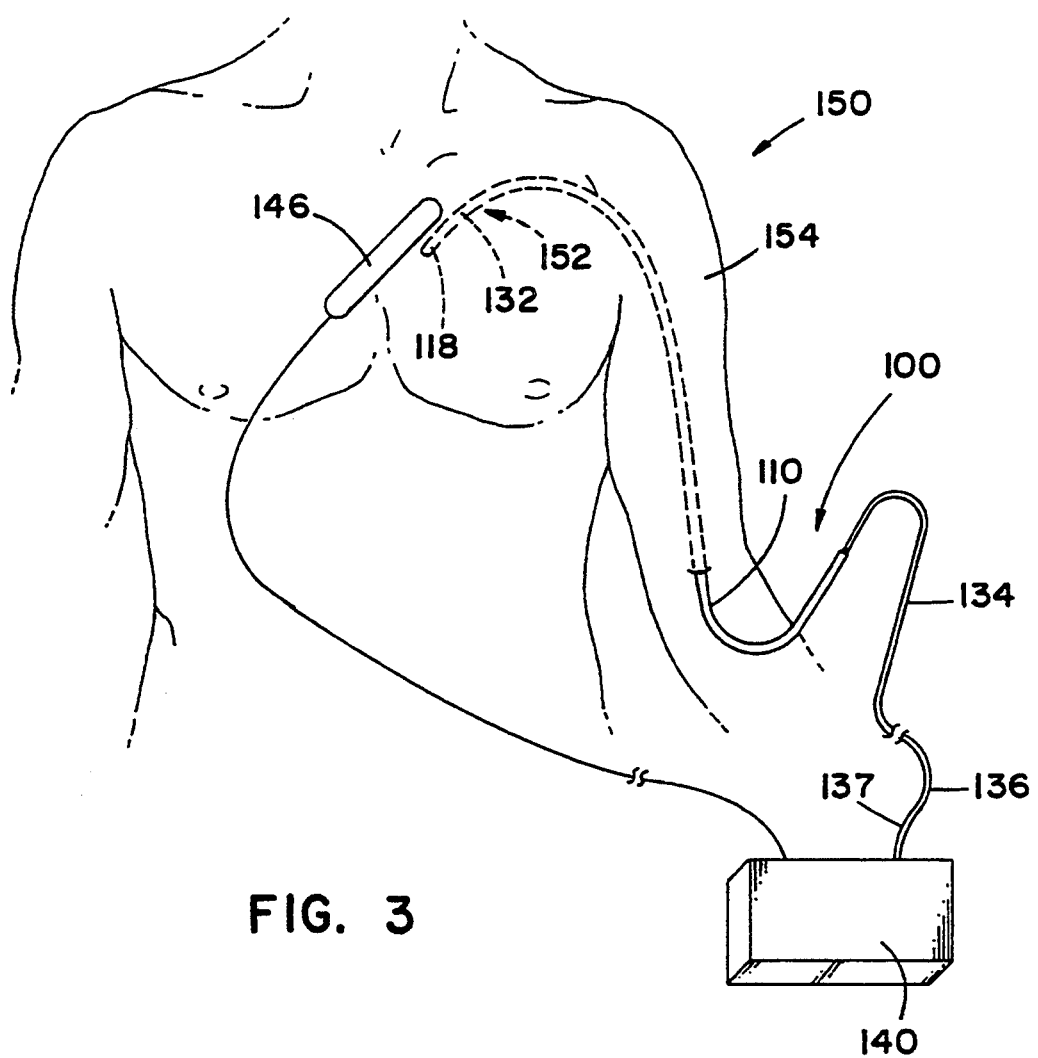
FIG. 3 is a depiction of the guide wire apparatus in use.

A first embodiment of the guide wire assembly in accordance with the invention is illustrated in FIGS. 1 through 3, and designated generally by the numeral 100. In general, the guide wire assembly 100 includes a J-shaped guide wire 110 and an internally-housed sensing member 120.

Referring to FIG. 1, guide wire 110 includes a proximal portion 114, a center portion 116, and a distal portion 118, a proximal end 115, a distal end 117. Guidewire 110 also includes a lumen 112 into which sensing member 120 is inserted. As shown in FIG. 2, sensing member 120 includes a metal core 122 that has a proximal section 124, a center section 126, and a distal section 128. As depicted, sensor element 132 is formed of a current conducting wire 134 wound around distal section 128 of metal core 122 in a double layer. As further illustrated, protective coating layer 135 covers sensing member 120 to protect sensor element 132 from damage. It is understood, however, that sensing member 120 need not be covered with protective coating layer 135.

Sensing member 120 is located within guide wire 110 so that distal section 128 with sensor element 132 are positioned in the area of center portion 116 at or near adjoining distal portion 118 of guide wire 110. A safety wire 113 may be housed within lumen 112 and attached to guide wire 110 at proximal end 115 and distal end 117.

Figure 4:
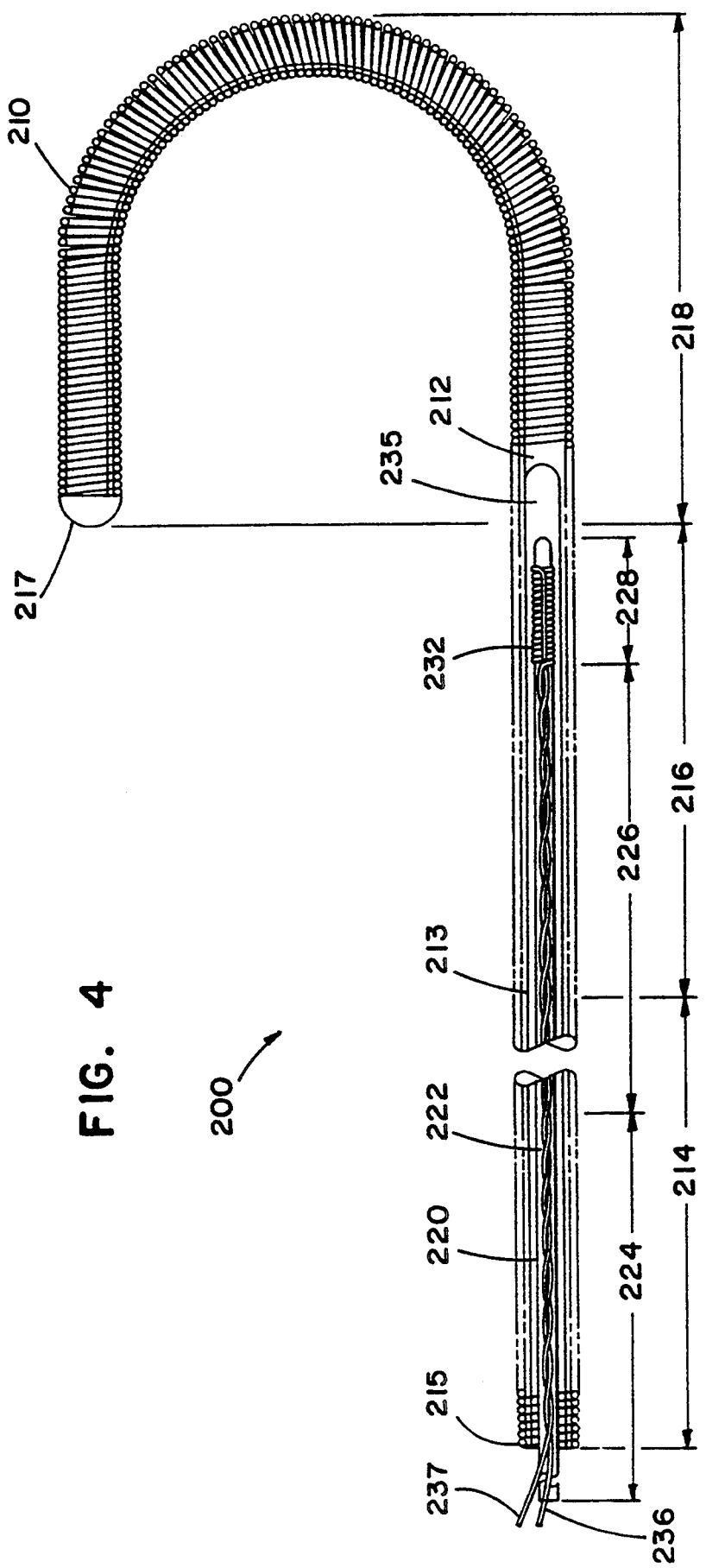
FIG. 4 is a fragmentary, cross-sectional side view of an alternative guide wire assembly in accordance with the present invention.

In the first embodiment depicted in FIGS. 1 and 2, center section 126 of metal core 122 is tapered so that the diameter of about its mid-point 130 is less than the diameter of either distal section 128 or proximal section 124 of the metal core 122. As illustrated in FIG. 4, in a second embodiment of a guide wire assembly, designated generally by the numeral 200, metal core 222 of sensing member 220 is not constricted at center section 226. Center section 226 provides a gradation in diameter from distal section 228 to proximal section 224 of metal core 222.

In use, as depicted in FIG. 3, guide wire apparatus 100 is inserted into the body of a patient 150, and advanced according to standard placement procedures to a desired location 152 where sensor element 132 may be detected. For example, guide wire apparatus 100 may be inserted into a blood vessel and advanced until an obstruction or constriction is sensed by touch, and the location of distal portion 118 of guide wire 110 detected. As depicted, current conducting wire 134 is connected by two lead wires 136, 137 to an electronic controller 140. To detect sensor element 132 of guide wire apparatus 100 in situ in the body, electronic controller 140 is activated to generate an alternating current to external field generator 146, positioned against the skin 154 of patient 150, which produces an electromagnetic (electromagnetic) energy field. The intersection of the electromagnetic energy field and sensor element 132 may be determined by measurement of the variation of signal amplitude as the field generator 146 nears the location of sensor element 132. The construction and arrangement of the electromagnetic energy field relative to sensor element 132, and the function for the signal amplitude determination follow the methods of Van Steenwyk in U.S. Pat. No. 4,173,228, the disclosure of which is incorporated herein by reference.

The interaction of the electromagnetic energy field and sensor element 132 may alternatively be determined by measurement of the phase transition of the current generated in sensor element 132 as the electromagnetic energy field moves over sensor element 132. In this embodiment, the construction and arrangement of the electromagnetic energy field relative to sensor element 132 and the function of the phase transition follow the method of Strohl et al. in U.S. Pat. No. 4,905,698 to Strohl et al.), the disclosure of which is incorporated by reference herein. Briefly, when field generator 146 is positioned to produce an electromagnetic energy field perpendicular to the long axis of sensor element 132, phase transition can be measured. As field generator 146 approaches sensor element 132, a voltage of a certain phase is produced in sensor element 132 by field generator 146. When field generator 146 is directly above sensor element 132, a phase transition occurs whereby no voltage is momentarily produced. As field generator 146 passes beyond sensor element 132, voltage is again produced but is completely out of phase with the earlier voltage or with the alternating current operating field generator 146. The phase transition produces a series of visual and/or audio signals to indicate location.

The construction of guide wire 110 and/or sensing element 132, advantageously provides a guide wire apparatus 100 that can internally house a location sensing device yet retain the flexibility and tactile response needed for maneuvering within branched systems, such as the vascular system, within the body of a patient similar to traditional guide wires. The guide wire apparatus of the invention, in general, is particularly useful in angioplasty or catheterization procedures, for detecting obstructions within a branched channels of a body system such as a blood vessel of a patient, and determining the location of the obstruction and distal end portion of the guide wire within such a body system.

The invention has been described with reference to various specific and preferred embodiments and techniques. However, it should be understood that many variations and modifications may be made while remaining within the spirit and scope of the invention.

What is claimed is:

1. A system suitable for invasive use and location determination in a patient, comprising:
   a guide wire having proximal, center and distal portions, and a lumen therethrough;
   a sensing member capable of detecting an externally-generated electromagnetic energy field, the sensing member including a metal core having distal, center and proximal sections, each section of the metal core further having an associated cross section, with at least a part of the associated cross section of the center section being of smaller dimension than the associated cross section of the distal and proximal sections, wherein said sensing member is housed within the lumen of the guide wire, the center section of the metal core is proximate to the center of the guide wire, and a current conducting wire is wound in a first layer around said distal end of said metal core to form a sensor element, and said sensor element is located near the distal portion of the guide wire;
   an externally-located means for generating a current within the sensor element; and,
   an externally-located means for detecting a current within the sensor element which is adapted for electrical connection with the sensor element.

2. A system according to claim 1, wherein the smaller dimension of the center section of the metal core provides a resiliency which mimics a resiliency of a guide wire without an internal sensor when invasively used with a patient.

3. A system according to claim 1, wherein at least part of the metal core comprises a stainless steel.

4. A system according to claim 3, wherein the metal core further comprises iron.

5. A system according to claim 1, wherein the conducting wire is a material selected from the group consisting of copper, palladium, silver, gold, platinum, or any combination thereof.

6. A system according to claim 1, wherein the sensor element further comprises a second layer of wire overlying said first layer.

7. A system according to claim 1, wherein the sensing member is coated with a flexible, non-toxic insulating material.

8. A system according to claim 7, wherein the sensing member is coated with a polymer material.

9. A system according to claim 8, wherein the polymer material is a polyester.

10. A system according to claim 8, wherein the polymer material is polyethylene, polyurethane, polyvinyl chloride, polyamide or tetrafluoroethylene.

11. A system according to claim 1, wherein the guide wire comprises a coiled wire.

12. A system according to claim 1, wherein the detecting means measures the amplitude of the signal generated in the sensor element.

13. A system according to claim 1, wherein the detecting means determines a phase transition of the signal generated in the sensor element.

14. A method of locating a guide wire apparatus in the body of a patient, comprising:
   (a) inserting a guide wire apparatus into the body, said apparatus being a combination of
      (i) a guide wire having proximal, center and distal portions, and a lumen therethrough; and
      (ii) a sensing member housed within said lumen of the guide wire, the sensing member including a metal core having distal, center and proximal sections, each section of the metal core further having an associated cross section, with at least a part of the associated cross section of the center section being of smaller dimension than the associated cross section of the distal and proximal sections, wherein the center section of the metal core is proximate to the center of the guide wire, and a current conducting wire is wound in a first layer around said distal end of said metal core to form a sensing element; said sensor element located near the distal portion of the guide wire;
   (b) advancing the guide wire apparatus to a location within the body
   (c) determining the location of the sensor element within the body of the patient by generating and detecting a current within the sensor element through application of an external magnetic field.

15. A method according to claim 14, wherein the smaller dimension of the center section of the metal core provides a resiliency for the guide wire housing the sensing member which mimics a resiliency of a guide wire without an internal sensor when inserted into the patient.

16. A method according to claim 14, comprising the additional step of sensing, by tactile response of the guide wire apparatus, the physical character of a portion of the body into which the guide wire apparatus is inserted, the tactile response being determined in part by the construction of the sensing member.

17. A method according to claim 16, wherein the sensing step includes locating an obstruction in a blood vessel of the patient.

18. A guide device suitable for invasive use in a patient, comprising:
   a guide wire having proximal, center, and distal portions and a lumen therethrough; and
   a sensing member housed within the lumen of the guide wire, and having distal, center and proximal sections, said center section of said sensing member proximate said center portion of said guide wire, each of said sections having an associated cross section, and a current conductor sensor element means which is located on the distal section for interacting with an externally-generated electromagnetic field so as to provide a current in the current conducting sensor element means, the associated cross section of the center section having at least in part a smaller dimension than the associated cross section of the distal and proximal sections.

19. A guide device according to claim 18 wherein the smaller dimension of the center section member is capable of providing at least in part to the guide device a tactile response and maneuverability comparable to that of a guide wire without an internal sensor when invasively used in a patient.

20. A guide device according to claim 18 wherein the sensing member comprises a metal core having distal, center and proximal sections; and
   a current conducting wire wound in a first layer around a part of the distal section of the metal core to form the current conducting sensor element means.

* * * * *